(12) United States Patent
Haszler et al.

(10) Patent No.: US 6,512,810 B1
(45) Date of Patent: Jan. 28, 2003

(54) METHOD OF ANALYZING A SPECIMEN COMPRISING A COMPOUND MATERIAL BY X-RAY FLUORESCENCE ANALYSIS

(75) Inventors: Alfred Johann Peter Haszler, Valendar (DE); Hormoz Ghaziary, Los Gatos, CA (US)

(73) Assignee: Corus Aluminium Walzprodukte GmbH, Koblenz (DE)

( * ) Notice: Subject to any disclaimer, the term of this patent is extended or adjusted under 35 U.S.C. 154(b) by 18 days.

(21) Appl. No.: 09/635,003

(22) Filed: Aug. 8, 2000

(30) Foreign Application Priority Data

Aug. 10, 1999 (EP) .......................................... 99202608.8

(51) Int. Cl.⁷ .............................................. G01N 23/22
(52) U.S. Cl. ........................................... 378/45; 378/50
(58) Field of Search .............................. 378/45, 46, 50, 378/48, 49

(56) References Cited

U.S. PATENT DOCUMENTS

| | | | |
|---|---|---|---|
| 2,711,480 A | | 6/1955 | Friedman |
| 4,696,023 A | | 9/1987 | Kuusi |
| 4,764,945 A | * | 8/1988 | Tadahiro .................... 378/50 |
| 5,113,421 A | * | 5/1992 | Gignoux et al. ............ 250/367 |
| 5,365,563 A | * | 11/1994 | Kira et al. .................... 378/44 |
| 6,173,037 B1 | * | 1/2001 | Brouwer ..................... 378/45 |

FOREIGN PATENT DOCUMENTS

| JP | 0389774 | 10/1990 |
|---|---|---|

OTHER PUBLICATIONS

European Search Report for Application No. 99202608.8.
Patent Abstracts of Japan, vol. 011, No. 362 (P–640), Nov. 26, 1987 & JP 62 137552 A ( Seiko Instr & Electronics Ltd), Jun. 20, 1987 *abstract*.
Patent Abstracts of Japan, vol. 011, No. 022 (P–538), Jan. 21, 1987 & JP 61 195335 A (Shimadzu Corp), Aug. 29, 1986 *abstract*.

* cited by examiner

Primary Examiner—Robert H. Kim
Assistant Examiner—Hoon K. Song
(74) Attorney, Agent, or Firm—Stevens, Davis, Miller & Mosher, LLP

(57) ABSTRACT

The invention relates to a method of analyzing a specimen comprising a compound material by X-ray fluorescence analysis wherein a beam of polychromatic primary X-rays is generated in an X-ray tube by conversion of electric current into X-rays, and said beam is directed at the specimen, and wherein the element specific fluorescent X-rays are selectively detected using means for detection and an intensity of said fluorescent X-rays is determined. After the electric current is applied to the X-ray tube and the intensity of element specific fluorescent X-rays is determined, a second intensity of the element specific fluorescent X-rays is determined while applying an electric current with a different value than the previous electric current, and at least the relative abundance of the chemical element present in the compound material is then determined using the values of both intensities. The thickness of the first layer can be determined simultaneously.

7 Claims, 3 Drawing Sheets

METHOD OF ANALYZING A SPECIMEN COMPRISING A COMPOUND MATERIAL BY X-RAY FLUORESCENCE ANALYSIS

FIELD OF THE INVENTION

The invention relates to a method of analysing a specimen comprising a compound material by X-ray fluorescence analysis wherein a beam of polychromatic primary X-rays is generated in an X-ray tube by conversion of electric current into X-rays, and said beam is directed at the specimen in which specimen the primary X-rays are converted into chemical element specific fluorescent X-rays, and wherein the element specific fluorescent X-rays are selectively detected using means for detection and an intensity of said fluorescent X-rays is determined.

For the purpose of this application, a compound material is a material that comprises a mixture of different chemical elements, such as an alloy in the case that the material is a metal.

BACKGROUND OF THE INVENTION

A method such as described above is known from U.S. Pat. No. 2,711,480. In the known method, a specimen of metal sheet comprising a backing and a thin layer covering the backing, is analysed using X-ray fluorescence analysis. During irradiation of the metal sheet with primary X-rays part of the primary X-rays are absorbed in the metal sheet and fluorescent X-rays are re-emitted by a chemical element that is comprised in the metal sheet. Some of these fluorescent X-rays are selectively detected. In order to determine the thickness of the thin layer, fluorescent X-rays re-emitted from a chemical element in the backing are selectively detected after they have passed through the thin layer. The fluorescent X-rays are partially absorbed in the thin layer. To determine the thickness of the thin layer, the measured intensity is compared to a reference intensity measured using a control specimen for the metal sheet whereon the thin layer is not present.

SUMMARY OF THE INVENTION

It is an object of the invention to provide a method for X-ray fluorescence analysis for determining at least the relative abundance of the chemical element in a specimen comprising a compound material. For the purpose of this patent application, the term relative abundance is used for the abundance of a chemical element in a compound material, expressed in percentage by weight.

It is an other object of the invention to provide a method for X-ray fluorescence analysis that can be combined in an easy way with the known method for determining the thickness of a thin layer covering a backing.

According to the invention, one or more of these objects is achieved by a method according to the first paragraph of this description, in which, after the electric current is applied to the X-ray tube and the intensity of element specific fluorescent X-rays is determined, a second intensity of the element specific fluorescent X-rays is determined while generating a second beam of primary X-rays using an electric current with a different value than the previous electric current, and at least the relative abundance of the chemical element present in the compound material is then determined using the values of both intensities.

The invention is based on the finding, that the ratio of the count rates in the case of two different tube currents during which application the X-ray fluorescence is detected, varies with the relative abundance (i.e. weight percentage) of the chemical element in the compound material. Therefore, the ratio of the determined intensities is a measure of the relative abundance of the chemical element in the compound material. Since this method of analysis comprises a relative measurement of intensities, the relative abundance of the chemical element can still be determined even though other factors may affect the absolute value of the intensities, such as the presence of an absorbing layer of material between the sheet and the means for detection.

It is believed that the ratio of the intensities of detected X-ray fluorescence in the case of two different tube currents, varies with the relative abundance of the chemical element in the compound material as a result of a change in the absorption characteristics of the initial polychromatic X-rays or the re-emitted fluorescent X-rays, or both. The relative abundance can easily be extracted from the measurement of the intensities by comparing to a calibration that is determined using control specimens of which the relative abundance of the chemical element has been established using an independent method such as a direct chemical analysis.

The second beam of primary X-rays may be generated using a second X-ray tube. However, it is preferred that the second beam of primary X-rays is generated with the same X-ray tube as the previous beam of primary X-rays. This is a cheap embodiment of the method. The one X-ray tube may be mounted stationary. This is relatively easy compared to instruments where angle of X-ray beam compared to the specimen can be varied, and furthermore there is no need to take into account any influence caused by different angles.

The method of analysis according to the invention can easily be combined with the known method for determining the thickness of a first layer on a second layer of material. In this case, the determined relative abundance of the chemical element is preferably used to calculate a reference X-ray fluorescence intensity to which at least one of the determined intensities is compared to determine the thickness of the first layer. Herewith it is achieved that the thickness of the first layer is determined by X-ray fluorescence analysis, without the need to separately measure the reference intensity of the control specimen without the first layer. The calibration contains the information that is required to calculate for each used X-ray tube electrical current the reference intensity of fluorescent X-rays once the relative abundance of the chemical element that is present in the specimen is determined.

In the case that the first layer comprises one or more sublayers, it is preferred that for each layer or sublayer in which the concentration of the chemical element is to be determined an additional intensity is determined of the selectively detected fluorescent X-rays while during this each time the electrical current is applied at a different value. From the thus determined intensities, it is possible to extract each relative abundance of the chemical element in each sublayer that is desired.

Preferably, a metal alloy is selected as the compound material, the metal alloy more preferably being an aluminium alloy, the aluminium alloy preferably containing a chemical alloy element of the group of Cu, Mn, Zn, Fe. Herewith the relative abundance of an alloying element that is often used within an aluminium alloy can be determined with a fast and cheap method that can be applied in a metal sheet production plant. Cu is frequently used as alloying element in aluminium products such as aluminium sheet. Cu is a fast diffusing element, that may redistribute in the product during various stages of production. Therefore, a method for non-destructive analysis of a specimen containing Cu is very important. The advantage of using the method according to the invention for analysis of Cu in aluminium sheet is that Cu is also a suitable X-ray fluorescence emitting element. For the purpose of this application, aluminium sheet is held to comprise aluminium alloy sheet.

BRIEF DESCRIPTION OF THE DRAWINGS

The invention will now be explained using an example of the method according to the invention applied to measuring the abundance of an alloying element in an aluminium alloy, with reference to the drawing where.

DETAILED DESCRIPTION OF THE PREFERRED EMBODIMENTS

Calibration is first performed to execute the method according to the invention. For each type of material and each experimental geometry including X-ray tube and detection efficiency, the calibration will be a unique one.

Figure 1:
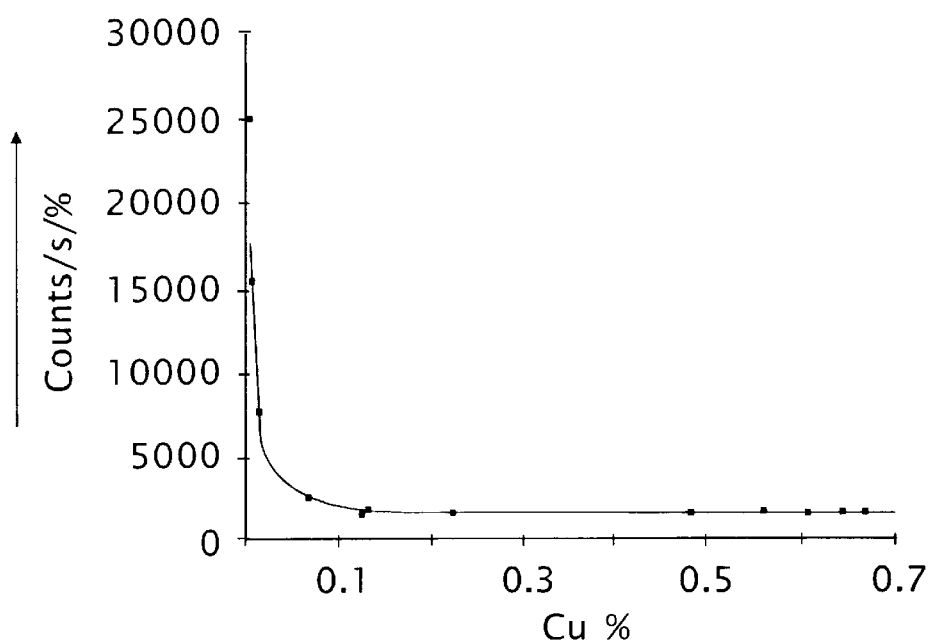
FIG. 1 shows an example of an experimentally determined sensitivity curve for Cu in aluminium.

FIG. 1 shows an experimentally determined sensitivity curve for Cu in aluminium as a function of %Cu. The sensitivity curve governs the relationship between fluorescent X-ray detection sensitivity and the weight fraction of the fluorescing element in question, or count rate per weight percent of the element (counts/s/%). The sensitivity curve was determined by using calibration specimens of aluminium each with a known weight fraction of Cu. A primary beam of X-rays was generated in an X-ray tube operated with a certain tube current, and Cu-specific $K_{60}$ X-rays were detected and the count rate thereof was determined. As can be seen in FIG. 1, the count rate per percentage of Cu in an aluminium alloy is approximately constant when the concentration of Cu exceeds approximately 0.2% and even more when the concentration of Cu exceeds 0.8%. However, a non-linear range begins when the concentration of Cu is lower than approximately 0.8%. The count rate per %Cu is observed to increase strongly below 0.2%. The drawn line in FIG. 1 is a fit to the equation of the form:

$$\text{Sensitivity} = a + b/\%,$$

where a and b are fit parameters, and % denotes the concentration of the fluorescing element.

A sensitivity curve such as shown in FIG. 1 may be used directly to determine the content of Cu in aluminium, to convert a measured count rate of Cu—$K_{60}$ X-ray fluorescence into a percentage of Cu. However, in many cases there exists an unknown amount of X-ray fluorescence absorbing material between the material from which the element-specific X-ray fluorescence originates and the means for detecting the element-specific X-ray fluorescence. In this case, since there is an additional unknown, another, independent measurement is required.

Such independent measurement is provided by repeating the above procedure while operating the X-ray tube at a different tube current. It is found that the ratio of the sensitivities determined for two different tube currents varies with the weight percentage of Cu in the aluminium layer. An example of this is shown in FIG. 2, where the ratio is shown of a fitted sensitivity curve (according to the equation Sensitivity=$a+b/\%$) to data measured while operating the X-ray tube at 4.5 mA and a fitted sensitivity curve to data obtained while operating the X-ray tube at 3.5 mA.

Figure 2:
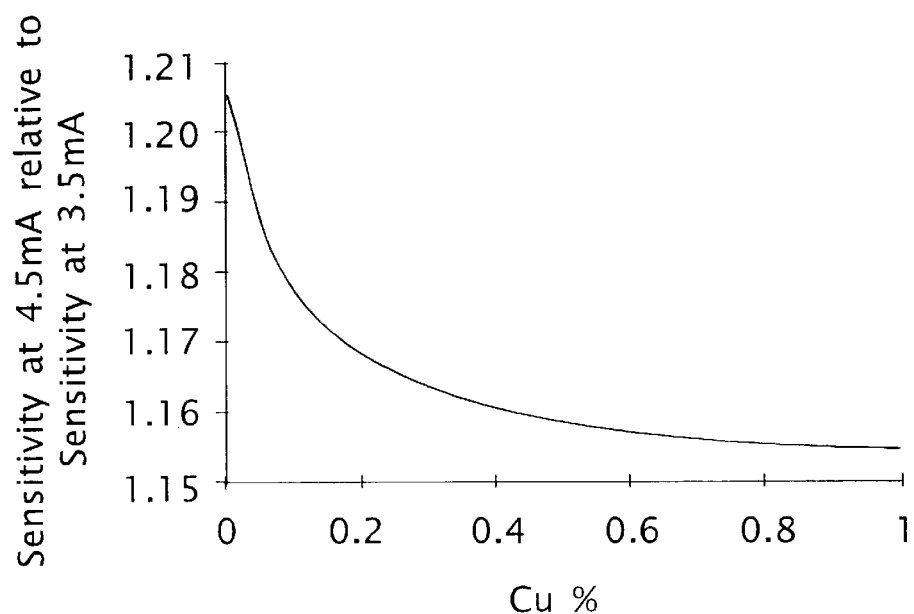
FIG. 2 shows an example of the ratio of two sensitivity curves as a function of the weight percentage of Cu in aluminium.

The ratio shown in FIG. 2 varies with the abundance of Cu that is present in the aluminium alloy. Therefore, changing the current with which the X-ray tube is operated provides the independent measurements which are required to determine the amount of the X-ray fluorescent element present in the material.

Figure 3:
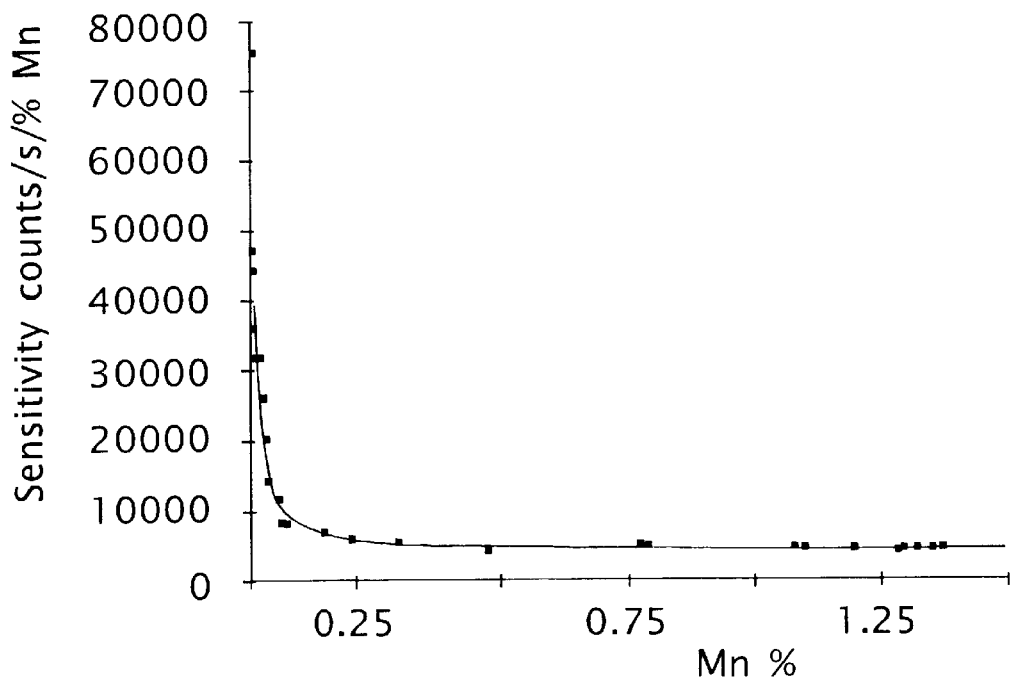
FIG. 3 an example of an experimentally determined sensitivity curve for Mn in aluminium.

The above described method for analysis of a specimen may be applied to a great variety of different materials and material systems. However, the method is particularly found of advantage in metal sheet production plants. In the case of aluminium specimens, Mn, Fe, and Zn are also good chemical elements for the above described method. FIG. 3 shows a sensitivity curve obtained for Mn in aluminium.

In a metal sheet manufacturing plant, quantitative information on the content of alloying elements in a metal sheet, in particular in an aluminium-alloy product, is typically only available from quantometer analysis of molten metal, in particular molten aluminium alloy, during a casting process. The chemistry obtained at this stage might not be valid for the final metal sheet producer instance, as a result of interdiffusion of alloying elements between different alloy layers during, for instance, a hot rolling operation or an annealing operation. Moreover, this analysis method is rather labour intensive and entails unacceptable long turn-around times of at least several hours.

Currently, an important product that comprises aluminium sheet material is brazing sheet. Brazing sheet is typically used in automobile radiators, air conditioner evaporators, heat exchangers, and the like. Brazing sheet is a composite material that comprises an aluminium alloy core, with a first layer on one or both sides comprising one or more sublayers with of different alloys, most often different aluminium alloys. The purpose of the cladding is to impart specific properties in the outside layer of a sheet product, such as brazing capability, corrosion resistance, erosion resistance, wear resistance, while the core alloy maintains other necessary properties such as strength.

Brazing sheet composite may be manufactured by hot rolling in which a slab of cladding material is placed to an ingot of the core material. The hot rolling process is then performed on this combination. In the final product the core and the cladding are strongly bond together, due to the fact that they are primarily of the same metal with a different content of alloying elements. Typically both core and cladding consist of over 80% aluminium. The process is highly delicate, and requires strict operation practices since the final sheet specification is usually rigid. Among the specifications which must be met is the cladding thickness as well as the total thickness of the brazing sheet.

In the art, there are two general methods of using XRF radiation to measure the thickness of sheet material or the thickness of a first layer of material on top of a second layer: (a) a method disclosed in U.S. Pat. No. 2,926,257 in which the intensity of fluorescence of the layer under analysis itself it approximately proportional to the thickness of that layer, and (b) a method disclosed in U.S. Pat. No. 2,711,480, in which the attenuation in the layer or sheet under investigation of fluorescence of an underlying layer or backing is a measure for the thickness. The method according to an embodiment of the invention is capable of following both, depending on the mathematics with which the measured intensities are processed and interpreted.

Figure 4:
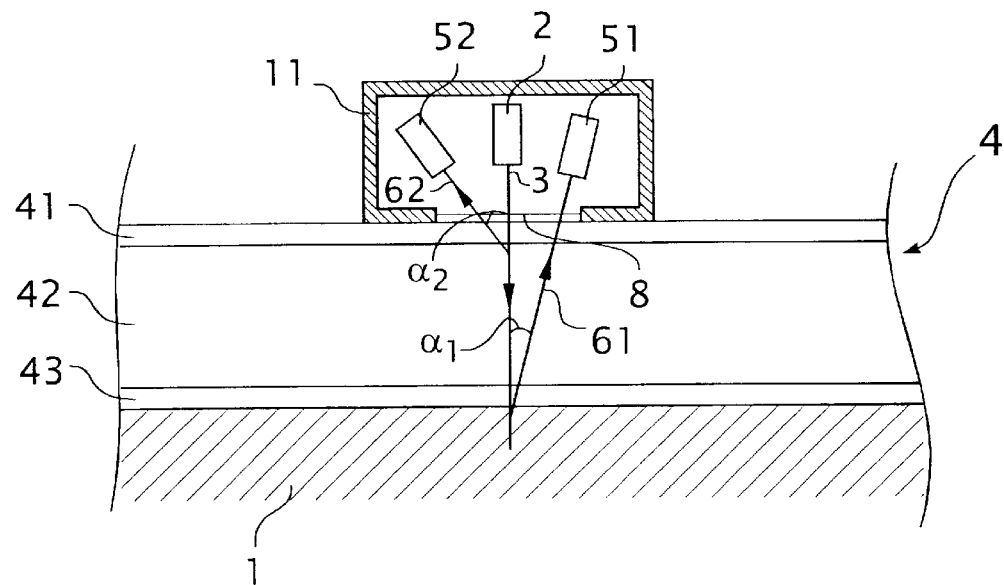
FIG. 4 shows a schematic cross sectional view of a measurement geometry according to an embodiment of the invention.

Referred now is to FIG. 4, which shows a schematic cross sectional view of a measurement geometry according to an embodiment of the invention. FIG. 4 shows an external specimen backing support (1), means (2) for generating and directing a primary beam of primary X-rays (3) on a specimen which is in this case a metal sheet (4), and means (51, 52) for detection and determination of an intensity of element specific fluorescent X-rays (61, 62), also known in the art as XRF, or X-ray induced fluorescence. The metal sheet is depicted in cross section, and its thickness is greatly exaggerated in the drawing, in order to make visible some of the layers within the sheet.

The means for directing the beam of primary X-rays, may comprise an X-ray source as conventionally known in the art. For instance, a 30 kV X-ray tube comprising a tungsten target has been found to provide an excellent source of polychromatic X-rays, suitable to excite fluorescent X-rays in most alloying elements in aluminium. The detecting means are placed such as to selectively receive the characteristic fluorescence of preselected elements. Element-specific fluorescence of elemental $K_{60}$ levels is usually quite suitable for this purpose.

The means for detecting fluorescent X-rays, and for measuring the intensity thereof, may be chosen according to what is generally known in the art. They may comprise a collimator, a dispersion crystal (such as LiF), and a proportional counting device. A detection channel comprising a sealed proportional counting tube is found to be very suitable. The means for directing and detecting X-rays may be comprised into a (translatable) integrated unit (11), furnished with an X-ray window (8).

Attenuation of X-rays in matter is quantified by published attenuation and absorption coefficients for specific materials and X-ray wavelengths. In general, attenuation of X-rays propagating over a certain distance is described by the law of Lambert-Beers. In order to extract a correct value for the layer thickness from an intensity ratio of XRF radiation before and after propagation through the layer, accurate chemical analysis of the metal sheet, and/or correct values for the absorption coefficient and density of the metal sheet are required For purposes of further explanation, it is assumed that the method according to the invention is applied to perform method (b). Referring to FIG. 4, the thickness of thickness of the first layer, or cladding 41, sandwiched between the second layer, or core 42, and an X-ray tube 2 and the means for detection 52, is thus derived from the attenuation within the ding 41 of X-ray fluorescent radiation (62) of a fluorescent element comprised in the second layer (42).

Laboratory measurements were performed to establish the fraction of X-ray fluorescence that is absorbed in a first layer of aluminium alloy over a certain thickness, i.e. the intensity ratio IF. Cu—$K_\alpha$ fluorescence measurements were performed on a series of aluminium brazing sheets with a second layer (42) comprising a Cu-containing alloy, and the intensity ratio of Mn—$K_\alpha$ fluorescence was determined as a function of thickness of the first layer 41. The thickness of the first layer was measured independently using a metallographic/optical method as set out above, and ranged from 0.038 to 0.13 mm. Then the intensity ratio was measured. For each test the thickness of the first layer was plotted in the graph shown in FIG. 5 against the intensity ratio. As can be seen, the intensity ratio for the studied thickness range varied from 2.5 to 27 in a smooth monotonic function. As can be seen, a thickness of 0.040 mm corresponds to IF of 3.8 while a thickness of 0.130 mm corresponds to an IF of 27.

Figure 6:
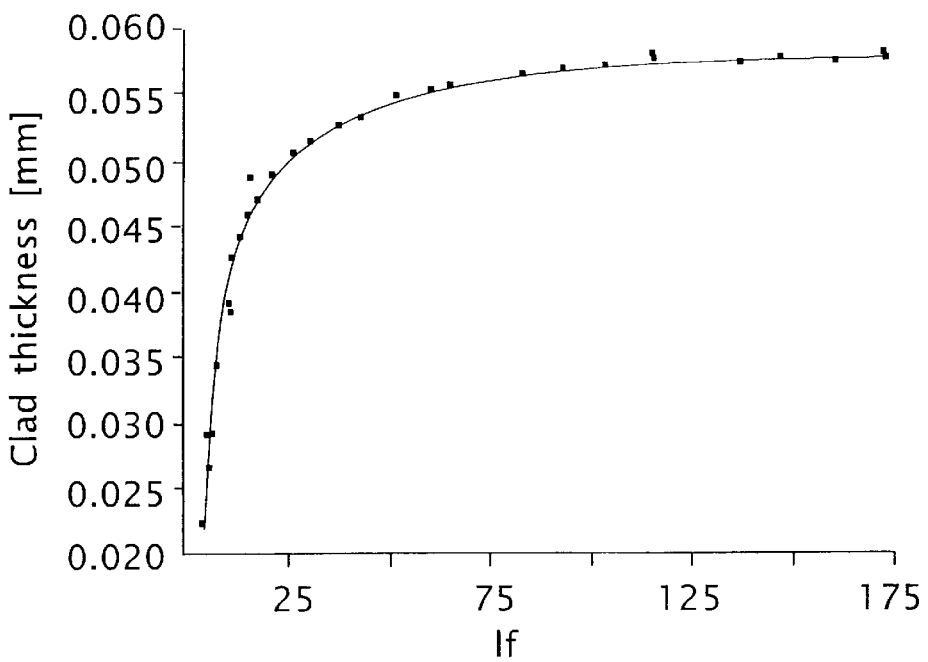
FIG. 6 shows an experimental relation between the intensity factor of Mn—$K_{60}$ fluorescent X-rays and thickness of a first layer in aluminium sheet.

FIG. 6 shows an example of calibration data for a first layer (41) thickness measured using a device according to the invention on a series of aluminium brazing sheets. In this case, a brazing sheet with a core (42) comprising a Mn-containing alloy was used, and the intensity ratio of Mn—$K_\alpha$ fluorescence was determined as a function of thickness of the first layer 41. A thickness of 0.022 mm corresponds to an IF of 4.0, while 0.057 mm corresponds to an IF of 175, and in between a monotonously varying behaviour was observed.

Figure 5:
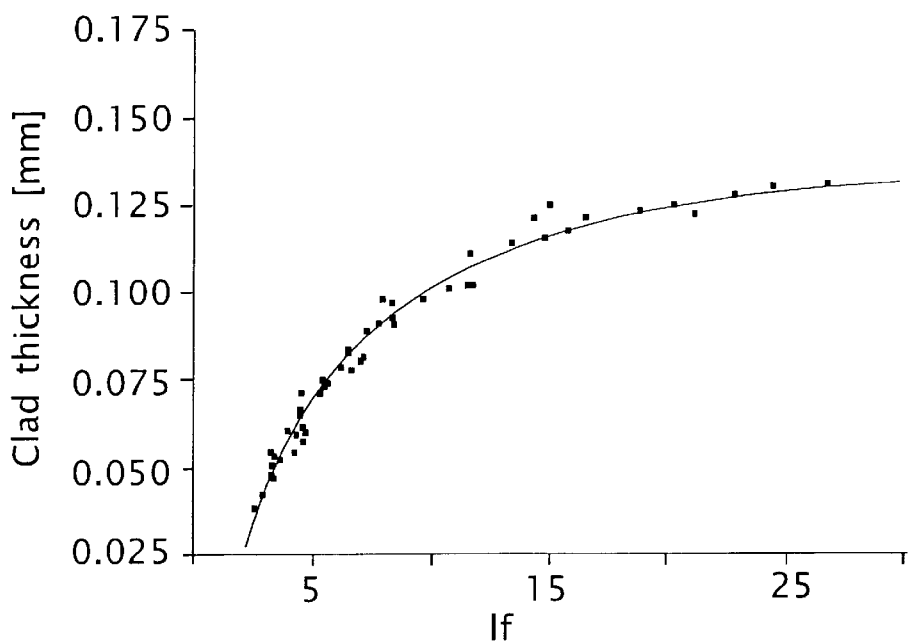
FIG. 5 shows an experimental relation between the intensity factor of Cu—$K_\alpha$ fluorescent X-rays and thickness of a first layer in aluminium sheet.

The drawn lines in FIGS. 5 and 6 are best fits according to an equation of the form $$\text{Thickness}=a\cdot\exp(b/IF),$$

in which a and b are experimentally determined parameters. This form describes the measured data quite satisfactory, as can be seen in FIGS. 5 and 6. Nevertheless, it is not excluded that other forms may be useful to describe this relationship between thickness and IF. For instance, an equation of the form $$\text{Thickness}=a+b\cdot\ln(IF)$$

has in many cases also been found useful to parametrise calibration data.

In a case that the first layer is free of the selected element-specific fluorescent element, there are two unknown parameters: the relative abundance of the fluorescent element in the second layer and the thickness of the first layer. The measured intensity of fluorescent X-rays depends on the amount of fluorescence that is emitted from the second layer, which obviously depends on the relative abundance of the chemical element, as well as on the intensity factor. These parameters can be extracted from two measurements at different tube currents according to the method of the invention, since they are independent measurements that lead to two equations with two unknowns.

In a case that the selected element-specific fluorescent element is comprised in more than one layer, the mathematics to analyse the measured fluorescence intensity ratios would comprise three independent equations each having three unknowns, i.e. thickness of the first layer, amount of the fluorescent element in the first and second layer. The method could for this case comprise applying three different current values to the X-ray tube, 3.0, 3.5, and 4.0 mA, to obtain three independent measurements of the fluorescence intensity of a fluorescing element comprised in the composite specimen. It will be understood that other values may be used. With the results of these measurements, the three independent equations can be solved, to yield values for the thickness of the first layer, and the amounts of fluorescent element in the first and second layers. For each independent measurement, a value for one unknown parameter can be extracted, for instance the thickness of a layer or the abundance of the fluorescent element.

As an example, a series of specimen as depicted in FIG. 4 were tested in the laboratory. The second layer (42) of each specimen was an aluminium alloy comprising Cu, and the aluminium first layer also comprised a low amount of Cu. Obviously, the Cu in both layers emit X-ray fluorescence. Referred is to the following table.

| A | B | C | D | E | F | G | H |
|---|---|---|---|---|---|---|---|
| 528579 | 0.56 | 2203 | 2635 | 0.061 | 0.061 | 0.049 | 0.033 |
| 525419 | 0.58 | 2230 | 2724 | 0.061 | 0.060 | 0.050 | 0.033 |
| 505922 | 0.11 | 1055 | 1260 | 0.078 | 0.086 | 0.012 | 0.009 |
| 527774 | 0.32 | 1454 | 1781 | 0.069 | 0.073 | 0.026 | 0.022 |
| 506515 | 0.56 | 2197 | 2686 | 0.058 | 0.059 | 0.049 | 0.033 |
| 502927 | 0.30 | 1261 | 1544 | 0.081 | 0.085 | 0.015 | 0.017 |
| 505165 | 0.31 | 1879 | 2314 | 0.059 | 0.051 | 0.067 | 0.025 |
| 527793 | 0.56 | 2005 | 2409 | 0.060 | 0.067 | 0.006 | 0.033 |
| 523561 | 0.07 | 1097 | 1333 | 0.067 | 0.071 | 0.022 | 0.012 |
| 507061 | 0.61 | 2223 | 2657 | 0.060 | 0.063 | 0.036 | 0.035 |
| 525881 | 0.09 | 1146 | 1383 | 0.066 | 0.070 | 0.023 | 0.013 |
| 527043 | 0.13 | 1285 | 1568 | 0.066 | 0.063 | 0.033 | 0.017 |
| 506517 | 0.55 | 2266 | 2757 | 0.059 | 0.057 | 0.048 | 0.033 |
| 527518 | 0.31 | 1535 | 1899 | 0.071 | 0.067 | 0.029 | 0.023 |
| 508503 | 0.48 | 1216 | 1467 | 0.097 | 0.105 | 0.020 | 0.017 |
| 522383 | 0.33 | 1444 | 1744 | 0.080 | 0.76 | 0.034 | 0.021 |
| 522828 | 0.33 | 1875 | 2332 | 0.047 | 0.052 | 0.048 | 0.025 |
| 524591 | 0.56 | 2176 | 2620 | 0.057 | 0.061 | 0.038 | 0.034 |
| 525907 | 0.61 | 1253 | 1510 | 0.101 | 0.111 | 0.015 | 0.019 |
| 585786 | 0.59 | 1445 | 1660 | 0.110 | 0.100 | 0.035 | 0.023 |

In the table, column A denotes a specimen identification number; column B the relative abundance of Cu (weight %) in the aluminium second layer as determined using quantometer analysis of the molten metal during the casting process; column C denotes the measured count rate (counts/s) with the X-ray tube operating at 3.5 mA; column denotes the measured count rate (counts/s) with the X-ray tube operating at 4.4 mA; column E denotes the thickness (mm) of the first layer as determined with cross sectional optical microscopy; column F denotes the thickness (mm) of the first layer as determined with the method of the invention; column G denotes the relative abundance of Cu (weight %) in the aluminium first layer as determined using quantometer analysis of the molten metal during the casting process; and column H denotes the relative abundance of Cu (weight %) in the aluminium first layer as determined with the method of the invention.

For this example, the method according to the invention is used to illustrate how the first layer thickness and the relative abundance of the fluorescent element in the first layer are determined. The results are compared to the relative abundance of Cu in the first layer that were determined using the quantometer analysis of the molten metal during the casting process, and the first layer thickness that were determined by cross sectional optical microscopy.

The intensity of X-ray fluorescence of the specimen was determined in the laboratory using the geometry as shown in FIG. 4, and column C shows the corresponding count rate while operating the X-ray tube at 3.5 mA, and column D shows the corresponding count rate while operating the X-ray tube at 4.5 mA.

From the count rate results and the calibration data, two independent equations were obtained for each specimen with two unknown parameters (the relative abundance of Cu in the second layer was accepted as known). After solving the equations, the parameters that were obtained are shown in columns F and H. As can be seen, the thickness is determined using the method according to the invention with an accuracy of about 0.005 mm.

The relative abundance of Cu in the first layer of the rolled metal sheet is found to deviate quite strongly from the quantrometric measurement of the molten metal: in some cases by a factor of up to 2. This relatively high deviation is possibly due to the fact that the amount of Cu in the clad is rather low compared to the amount of Cu in the second layer, possibly combined with the fact that Cu may have redistributed between the layers during the rolling process. It shows the importance of the method according to the invention.

The method according to the invention may be used for determination of several sublayer compositions, as well. For this an operator would select an appropriate fluorescent element for each sublayer in the first layer, depending on for instance the relative abundance of the fluorescent elements in every sublayer. Then after determining the intensity of fluorescence from each sublayer, the thickness of the sublayers above that layer can be extracted using the calibration curves. Different current settings can be applied to the X-ray tube to obtain a sufficient number of equations for the measurement of composition and thickness of each layer.

What is claimed is:

1. A method of analysing a specimen comprising a compound material by X-ray fluorescence analysis wherein a beam of polychromatic primary X-rays is generated in an X-ray tube by conversion of electric current into X-rays, and said beam is directed at the specimen in which specimen the primary X-rays are converted into chemical element specific fluorescent X-rays, and wherein the element specific fluorescent X-rays are selectively detected using means for detection and an intensity of said fluorescent X-rays is determined, and wherein, after the electric current is applied to the X-ray tube and the intensity of element specific fluorescent X-rays is determined, a second intensity of the element specific fluorescent X-rays is determined while generating a second beam of primary X-rays using an electric current with a different value than the previous electric current, and at least the relative abundance of the chemical element present in the compound material is then determined using the values of both intensities.

2. The method according to claim 1, wherein the second beam of primary X-rays is generated with the same X-ray tube as the previous beam of primary X-rays.

3. The method according to claim 1, wherein the specimen comprises a first layer on a second layer of material, and the determined relative abundance of the chemical element is used to calculate a reference X-ray fluorescence intensity to which at least one of the determined intensities is compared to determine the thickness of the first layer.

4. The method according to claim 3, wherein the first layer comprises one or more sublayers for each layer or sublayer in which the concentration of the chemical element is to be determined an additional intensity is determined of the selectively detected fluorescent X-rays while during this each time the electrical current is applied at a different value.

5. The method according to claim 1, wherein the compound material is a metal alloy.

6. The method according to claim 1, wherein the compound material is an aluminium alloy.

7. The method according to claim 1, wherein the compound material is an aluminium alloy containing at least one element selected from the group consisting of Cu, Mn, Zn and Fe.

* * * * *